US008620978B2

(12) United States Patent
Koyrakh

(10) Patent No.: US 8,620,978 B2
(45) Date of Patent: Dec. 31, 2013

(54) SYSTEM AND METHOD FOR FILTERING ELECTROPHYSIOLOGICAL SIGNALS

(75) Inventor: Lev A. Koyrakh, Plymouth, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1347 days.

(21) Appl. No.: 12/347,090

(22) Filed: Dec. 31, 2008

(65) Prior Publication Data
US 2010/0164612 A1 Jul. 1, 2010

(51) Int. Cl.
*H03B 1/04* (2006.01)

(52) U.S. Cl.
USPC ........... 708/300; 708/301; 708/302; 600/509; 600/544; 382/131; 382/265; 327/552; 327/556; 327/557

(58) Field of Classification Search
USPC .................. 327/556, 552, 557; 708/300–302; 382/265, 131; 600/509, 544
See application file for complete search history.

(56) References Cited

U.S. PATENT DOCUMENTS

| 4,641,649 | A | 2/1987 | Walinsky et al. |
|---|---|---|---|
| 4,892,102 | A | 1/1990 | Astrinsky |
| 4,945,912 | A | 8/1990 | Langberg |
| 5,122,137 | A | 6/1992 | Lennox |
| 5,188,117 | A | 2/1993 | Steinhaus et al. |
| 5,246,438 | A | 9/1993 | Langberg |
| 5,540,681 | A | 7/1996 | Strul et al. |
| 5,573,533 | A | 11/1996 | Strul |
| 5,584,830 | A | 12/1996 | Ladd et al. |
| 5,662,108 | A | 9/1997 | Budd et al. |
| 5,697,377 | A | 12/1997 | Wittkampf |
| 5,755,760 | A | 5/1998 | Maguire et al. |
| 5,820,568 | A | 10/1998 | Willis |
| 6,277,077 | B1 | 8/2001 | Brisken et al. |
| 6,383,151 | B1 | 5/2002 | Diederich et al. |
| 6,741,739 | B1 | 5/2004 | Vincent |
| 7,155,007 | B1 * | 12/2006 | Upton ...................... 379/392.01 |
| 7,599,570 | B2 * | 10/2009 | Berkner ........................ 382/265 |

(Continued)

FOREIGN PATENT DOCUMENTS

WO    WO 2000/011662    3/2000

OTHER PUBLICATIONS

Reeves, T.H., Jernigan, M.E., "Multiscale-based image enhancement", Electrical and Computer Engineering, 1997. IEEE 1997 Canadian Conference on, May 25-28, 1997, vol. 2, on pp. 500-503 vol. 2, ISBN: 0-7803-3716-6.*

(Continued)

*Primary Examiner* — Tammara Peyton
(74) *Attorney, Agent, or Firm* — Wiley Rein LLP

(57) ABSTRACT

An acquired signal indicative of electrophysiological activity is filtered using both a wavelet filter and either a notch filter or a band-pass filter to eliminate noise or interference, such as power line interference. A wavelet transform is used to transform the acquired signal into the wavelet domain, where a wavelet filter is applied to extract a soft component (e.g., a component with small wavelet coefficients). A filter, such as a notch filter or a band-pass filter, is applied to the soft component in order to isolate an interference signal. The interference signal is used to produce an output signal representing the acquired signal filtered to eliminate the interference signal. For example, the interference signal may be subtracted from the acquired signal. Alternatively, the output signal may be reconstructed from respective hard and soft components of the acquired signal as transformed into the wavelet domain.

32 Claims, 5 Drawing Sheets

(56) References Cited

U.S. PATENT DOCUMENTS

| | | | |
|---|---|---|---|
| 7,672,717 B1* | 3/2010 | Zikov et al. | 600/544 |
| 8,139,835 B2* | 3/2012 | Borsdorf | 382/131 |
| 8,165,849 B2* | 4/2012 | Mannar et al. | 702/189 |
| 2005/0137478 A1 | 6/2005 | Younge et al. | |
| 2007/0038382 A1 | 2/2007 | Keenan | |
| 2007/0129639 A1* | 6/2007 | Zhang et al. | 600/509 |
| 2008/0082018 A1 | 4/2008 | Sackner et al. | |
| 2008/0232665 A1 | 9/2008 | Borsdorf | |
| 2010/0010364 A1* | 1/2010 | Verbitskiy | 600/544 |
| 2012/0095357 A1* | 4/2012 | Tran | 600/509 |

OTHER PUBLICATIONS

International Search Report for PCT/US09/69398 dated Feb. 25, 2010.

Koyrakh, L., "Wavelet—notch filter combination for filter ringing elimintion", St. Jude Medical, St. Paul, MN, May 5, 2008.

Koyrakh, L.A., "Wavelet Transform Based Algorithms for EGM Morphology Discrimination for Implantable ICDs", Proceedings of Computers in Cardiology Conference, 26:343-346, 1999.

Limacher, R., "Removal of Power Line Interference from the ECG Signal by an Adaptive Digital Filter", ETC 96, Proc. of Europe Telemetry Conf.—Garmisch-Part., May 21-23, 1996.

McManus, C. D. et al., "Characterization and Elimination of AC Noise in Electrocardiograms: A Comparison of Digital Filtering Methods", Computers in Biomedical Research, 26:48-67, 1993.

Van Alste, J.A. et al., "Removal of Base-Line Wander and Power-Line Interference from the ECG by an Efficient FIR Filter with a Reduced Number of Taps", IEEE Trans. on Biomed. Eng., BME-32, (12):1052-1060, Dec. 1985.

Levkov, C. et al., "Removal of Power-Line Interference from the ECG: A Review of the Subtraction Procedure", Biomed Eng. Online. 4:50, 2005.

Matlab Software, May 5, 2008.

\* cited by examiner

SYSTEM AND METHOD FOR FILTERING ELECTROPHYSIOLOGICAL SIGNALS

BACKGROUND OF THE INVENTION a. Field of the Invention

The instant invention relates to filtering of noise in an electrical signal. In particular, the instant invention relates to systems and methods for filtering power line noise from acquired electrophysiological signals, such as ECGs and EGMs.

b. Background Art

Electrophysiology is the study of the electrical properties of and electrical activity in biological cells and tissues, such as the electrical activity that causes a heart to beat. Electrophysiological signals can be acquired and studied in a number of ways, including via electrocardiogram ("ECG") and electrogram ("EGM").

Power line interference, which may consist of one or more harmonics, is one source of noise that may contaminate ECG and EGM signals. Notch filters (band-stop filters with narrow stop bands) are often used to filter power line interference out of ECG and EGM signals. For example a notch filter with a stop band between about 59 Hz and about 61 Hz may be used to filter out interference from a 60 Hz power line typically used in the United States. Likewise, a notch filter with a stop band between about 49 Hz and about 51 Hz may be used to filter out interference from a 50 Hz power line typically used in Europe.

When applied to signals having sharp edges, such as ECG and EGM signals, notch filters may cause an undesirable "ringing effect." Ringing results from sudden changes in the acquired signal (e.g., the ECG or EGM signal) interacting with the notch filter, and typically manifests itself as wild oscillations at the notch filter central frequency (e.g., about 60 Hz in the United States and about 50 Hz in Europe).

Remedies have been suggested to eliminate the ringing effect, including the use of signal segmentation for special treatment of the sharp regions of the ECG or EGM signal and adaptive filters using the power line signal as a reference. Many of these remedies are computationally expensive and are therefore less desirable for use in systems that provide real-time analysis of electrophysiological data.

BRIEF SUMMARY OF THE INVENTION

An object of the present invention is to provide computationally-efficient methods for removing noise from an acquired electrophysiological signal, such as an ECG or EGM.

Another object of the present invention is to provide methods and systems that eliminate noise from an acquired electrophysiological signal, such as an ECG or EGM, without introduction of ringing artifacts.

Still another object of the present invention is to provide filtering methods and systems capable of simultaneously processing a large number of signals.

The present invention provides a method of filtering an electrophysiological signal including the following steps: acquiring a signal indicative of electrophysiological activity; applying a wavelet transform to transform the acquired signal into the wavelet domain; applying a wavelet filter to separate the transformed signal into a hard component and a soft component; reconstructing the hard component into the time domain; reconstructing the soft component into the time domain; and combining the reconstructed hard component and the reconstructed soft component into an output signal. The wavelet transform utilized may utilize Haar wavelets or CDF (5,3) wavelets.

Optionally, the method may also include applying a filter, preferably a notch filter, to the soft component. The notch filter may be applied to the reconstructed soft component (e.g., in the time domain) or, alternatively, to the soft component in the wavelet domain.

In some embodiments of the invention, the step of applying a wavelet filter to separate the transformed signal includes: determining a separation threshold; assigning portions of the transformed signal having wavelet coefficients above the separation threshold into the hard component; and assigning portions of the transformed signal having wavelet coefficients below the separation threshold into the soft component. The separation threshold may be determined based upon a statistical property of either the acquired signal or the transformed signal.

For example, the separation threshold may be determined based upon a moving average of the standard deviation of the transformed signal, and a signal window within which the moving average of the standard deviation is calculated may be about two cardiac cycles wide.

As another example, the separation threshold may be determined based upon a moving average of the wavelet coefficients, such as an exponential moving average of the wavelet coefficients where a forgetting factor of the exponential moving average is selected such that an effective window within which the exponential moving average is calculated is at least about two seconds wide.

In still other embodiments of the invention, the separation threshold may be determined based upon a moving average of the area under the curve of the transformed signal multiplied by a forgetting factor, which may be about 10.

Optionally, the method includes compensating for latency introduced by at least one filter, such as a wavelet filter applied to separate the transformed signal into the hard and soft components, a notch filter applied to the soft component, or any other desirable filter. This may be accomplished, for example, by applying a latency delay to the reconstructed hard component prior to combining the reconstructed hard component and the reconstructed soft component.

According to another aspect of the present invention, a method of filtering an electrophysiological signal includes the following steps: acquiring a signal indicative of electrophysiological activity; applying a wavelet transform to transform the acquired signal into the wavelet domain; applying a wavelet filter to separate the transformed signal into a hard component and a soft component; applying a notch filter to the soft component; and combining the hard component and the filtered soft component into an output signal.

In still another aspect, the present invention provides a method of filtering an electrophysiological signal including the following steps: acquiring a signal indicative of electrophysiological activity; applying a wavelet transform to transform the acquired signal into the wavelet domain; applying a wavelet filter to extract a soft component from the transformed signal; applying a filter to the soft component to isolate an interference signal; and producing an output signal comprising the acquired signal filtered to eliminate the interference signal. Optionally, at least one of the interference signal and the acquired signal may be adjusted such that the interference signal and the acquired signal are in phase.

It is contemplated that the step of applying a filter to the soft component to isolate an interference signal may include applying a band-pass filter to the soft component to produce the interference signal, while the step of producing an output signal may include subtracting the interference signal from the acquired signal.

It is also contemplated that the step of applying a filter to the soft component to isolate an interference signal may include applying a notch filter to the soft component and subtracting an output of the notch filter from the soft component to produce the interference signal, while the step of producing an output signal may include subtracting the interference signal from the acquired signal.

In still other embodiments of the invention, it is contemplated that the step of applying a wavelet filter to extract a soft component from the transformed signal may also include extracting a hard component from the transformed signal. The step of applying a filter to the soft component to isolate an interference signal may then include applying a notch filter to the soft component, while the step of producing an output signal may include combining the hard component with the filtered soft component.

Also disclosed herein is a method of filtering an electrophysiological signal including the following steps: acquiring a signal indicative of electrical activity in cardiac tissue; applying a wavelet transform to transform the acquired signal into the wavelet domain; applying a wavelet filter to extract a soft component from the transformed signal; applying a filter to the soft component to extract an interference signal; adjusting the interference signal to be in phase with the acquired signal; and subtracting the adjusted interference signal from the acquired signal to produce an output signal.

The filter applied to the soft component may be a band-pass filter or, in the alternative, a notch filter. In addition, the steps of applying a filter to the soft component to extract an interference signal and adjusting the interference signal to be in phase with the acquired signal may be repeated for each of a plurality of harmonics of the interference signal.

The present invention also provides a system for filtering an electrophysiological signal/ The system generally includes: a signal acquisition device configured to acquire a signal indicative of electrophysiological activity; a wavelet transformation processor that transforms the acquired signal into the wavelet domain; a first filtering processor that extracts a soft component from the transformed signal; a second filtering processor that isolates an interference signal; and a signal reconstruction processor that produces an output signal comprising the acquired signal filtered to eliminate the interference signal. The second filtering processor may apply a band-pass filter to the transformed signal and output the interference signal. Alternatively, the second filtering processor may apply a notch filter to the soft component of the transformed signal, subtract an output of the notch filter from the soft component of the transformed signal, and output the interference signal.

Optionally, the system further includes a third filtering processor that extracts a hard component from the transformed signal. This configuration permits the second filtering processor to apply a notch filter to the soft component of the transformed signal such that the signal reconstruction processor can combine the hard component of the transformed signal with the notch filtered soft component.

An advantage of the present invention is that it provides computationally-efficient methods and systems for filtering noise, such as power line interference, from electrophysiological signals.

Another advantage of the present invention is that it provides filtering methods and systems that can be used for simultaneous processing of large numbers of signals.

Still another advantage of the present invention is that it eliminates noise, such as power line interference, from electrophysiological signals with minimal introduction of ringing artifacts.

The foregoing and other aspects, features, details, utilities, and advantages of the present invention will be apparent from reading the following description and claims, and from reviewing the accompanying drawings.

DETAILED DESCRIPTION OF THE INVENTION

The present invention provides methods and systems for filtering noise, such as power line interference, from an electrical signal, such as a signal indicative of electrophysiological activity, while minimizing ringing artifacts. For purposes of this description, the invention will be described in connection with filtering the noise caused by a 60 Hz power line from an acquired ECG or EGM signal. One of ordinary skill in the art will appreciate, however, that the principles disclosed herein can be applied to good advantage to filter noise at any frequency from any signal.

Figure 1A:
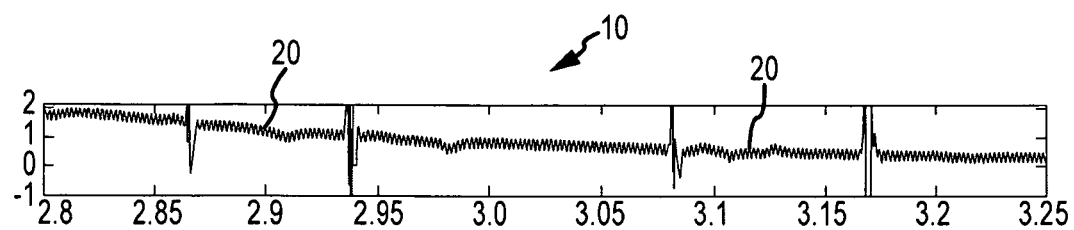
FIG. 1a is a representative electrogram exhibiting 60 Hz power line interference.
Figure 1B:
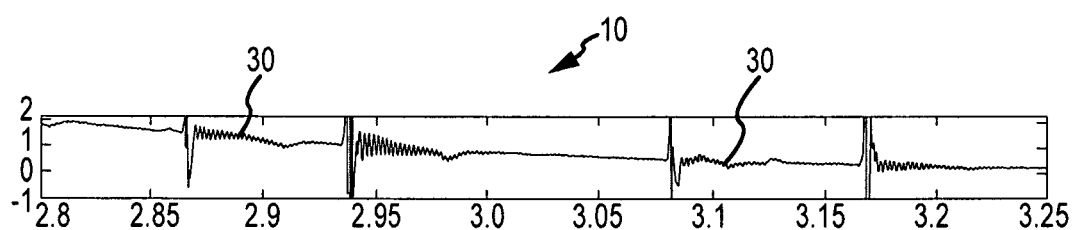
FIG. 1b depicts the electrogram of FIG. 1a after application of a 60 Hz notch filter exhibiting ringing artifacts.

FIG. 1a depicts a representative electrogram 10 as measured by an intracardiac electrode, for example during an atrial fibrillation ("AF") procedure. Electrogram 10 exhibits noise 20 due to interference from the 60 Hz power line powering the intracardiac electrode. FIG. 1b depicts electrogram 10 after application of a 60 Hz notch filter. Ringing artifacts 30 are visible following the sharp spikes in electrogram 10.

Figure 2:
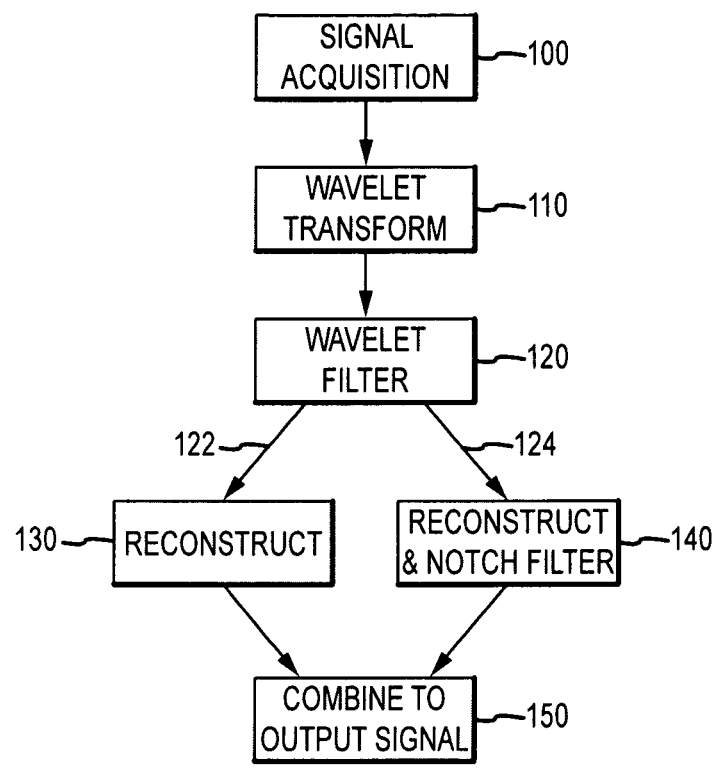
FIG. 2 is a flowchart illustrating the general steps of wavelet filtration and notch filtration according to an embodiment of the present invention.

A method of filtering a signal according to one embodiment of the present invention will be generally described with reference to FIG. 2.

In step 100, a signal indicative of electrophysiological activity is acquired, for example as an ECG or EGM similar to that shown in FIG. 1a.

In step 110, the acquired signal is transformed into the wavelet domain via application of a discrete wavelet transform.

Figure 1C:
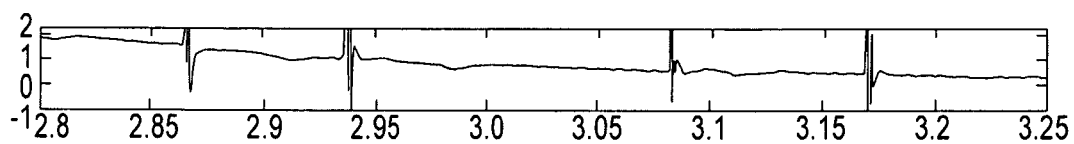
FIG. 1c depicts the hard component of the electrogram of FIG. 1a after wavelet filtration.
Figure 1D:
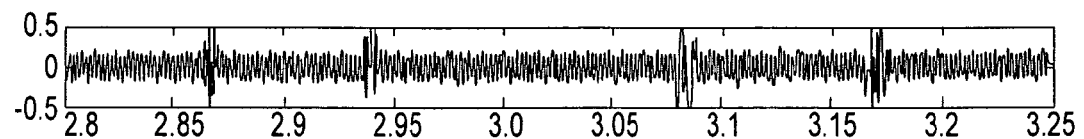
FIG. 1d depicts the soft component of the electrogram of FIG. 1a after wavelet filtration.

In step 120, a wavelet filter is applied to the transformed signal. The wavelet filter separates the transformed signal into a "hard" (or "sharp") component (line 122) and a "soft" (or "smooth") component (line 124). One of ordinary skill in the art will recognize that the hard component has relatively higher wavelet coefficients, while the soft component has relatively lower wavelet coefficients (which would typically be set to zero in the wavelet domain). FIGS. 1c and 1d illustrate, respectively, the hard and soft components of electrogram 10 depicted in FIG. 1a.

One possible interpretation of wavelet coefficients is slew rate. Thus, the hard component of the transformed signal generally corresponds to those portions of the acquired signal that are changing rapidly, while the soft component of the transformed signal generally corresponds to those portions of the acquired signal that are changing more gradually. The process of dividing the transformed signal into the hard and soft components is described in further detail below.

In step 130, the hard component of the transformed signal is reconstructed into the time domain.

Figure 1E:
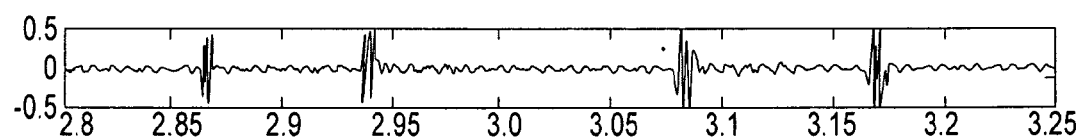
FIG. 1e depicts the soft component of FIG. 1d after application of a 60 Hz notch filter.

In step 140, the soft component of the transformed signal is both reconstructed into the time domain and filtered using a notch filter. For example, where it is desired to eliminate 60 Hz power line noise, a 60 Hz notch filter (e.g., a filter with a stop band from about 59 Hz to about 61 Hz) can be applied to the soft component. Preferably, the notch filter is applied to the soft component after reconstruction of the soft component into the time domain. It is contemplated, however, that the notch filter may instead be applied to the soft component before reconstruction thereof (e.g., in the wavelet domain). Applying the notch filter in the wavelet domain may also allow filtering of noise other than that due to power line interference. FIG. 1e illustrates the result of applying a 60 Hz notch filter to the soft component depicted in FIG. 1d.

Thus, the hard component and soft component of the transformed signal are separately reconstructed into the time domain. In addition, because the notch filter is applied only to the soft component, which does not contain the sharp edges that typically lead to ringing, the notch filter applied in step 140 does not produce significant ringing artifacts.

Figure 1F:
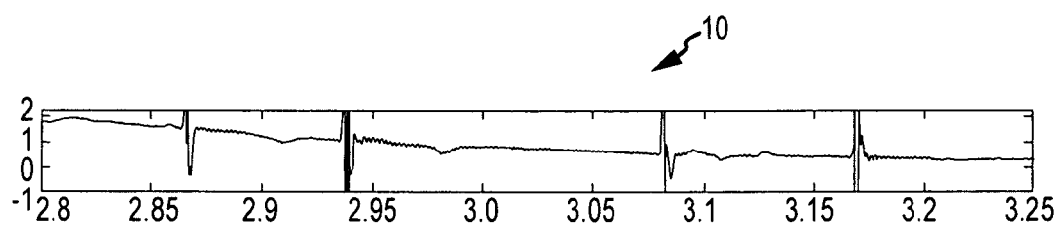
FIG. 1f depicts the electrogram of FIG. 1a after being wavelet filtered and notch filtered according to an embodiment of the present invention.

In step 150, the reconstructed hard component and the notch filtered and reconstructed soft component are combined into an output signal. The output signal represents the acquired signal filtered to eliminate an interference signal, which, in the embodiment described above and illustrated in FIGS. 1a-1f, is the 60 Hz power line noise. FIG. 1f depicts electrogram 10 after application of the method depicted in FIG. 2 and illustrates the substantial elimination of noise 20 and the substantial absence of ringing artifacts 30 advantageously provided by the present invention.

Figure 3:
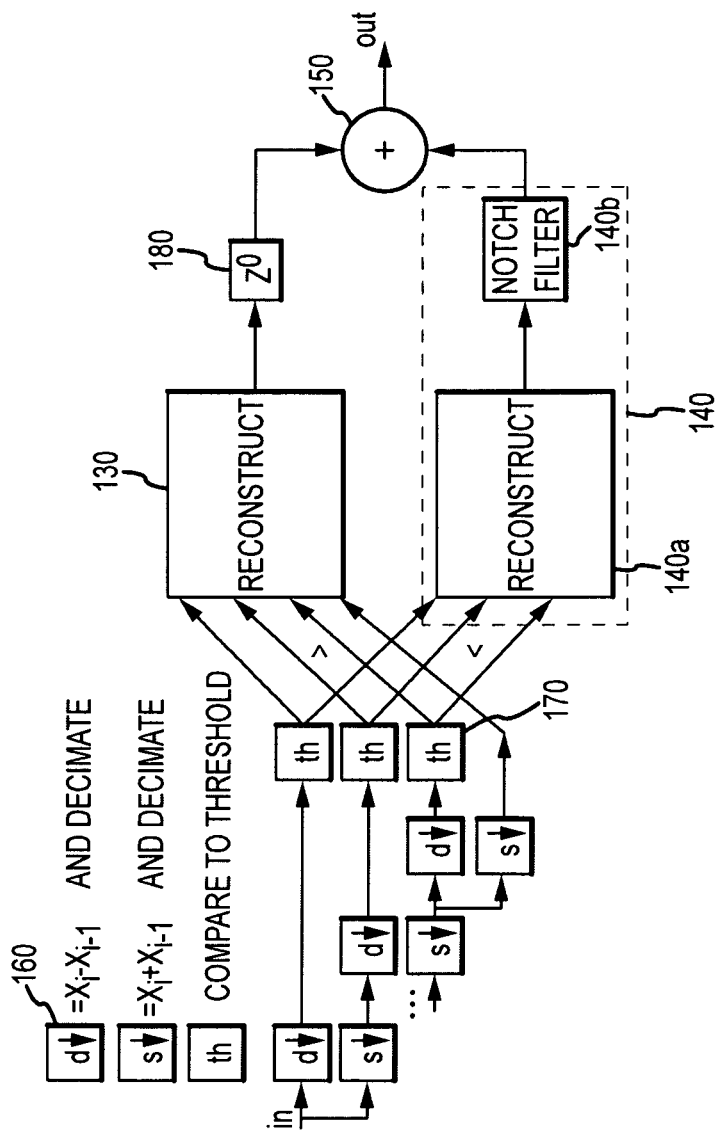
FIG. 3 is a block diagram of one embodiment of a wavelet filtration and notch filtration method according to the present invention.

FIG. 3 is a block diagram of a method of filtering a signal according to the present invention. Specifically, FIG. 3 illustrates the use of Haar wavelets for the wavelet transformation. Of course, other wavelet bases, including CDF (5,3) ("linear") wavelets, may be suitable for use in the present invention. Haar and CDF (5,3) wavelets are particularly preferred because they have sharp edges and the smallest number of vanishing moments, and therefore facilitate splitting the transformed signal into the hard and soft components.

The number of wavelet transform stages (e.g., the filter bank illustrated at the left-hand side of FIG. 3 and described below) is preferably determined based on an efficient coupling of the corresponding time scales to the frequency of the interference signal. For example, if the input signal sampling frequency is 1200 Hz, and the interference signal to be filtered is a 60 Hz power line signal, then, during one period of the power line signal, 20 samples are taken. Because the length of the frame for the wavelet transform is a power of 2, the minimum number of wavelet transform stages that efficiently couple to the 60 Hz interference signal is 5, which corresponds to a buffer size of 32 samples. One of ordinary skill in the art will recognize that different wavelet bases have different frequency domain properties, with smoother wavelet bases having effectively narrower Fourier spectra. Thus, one of ordinary skill in the art will recognize that the use of Haar wavelets may require a greater number of wavelet transform stages than, for example, CDF (5,3) wavelets.

Another consideration that may be taken into account in choosing a suitable wavelet basis is the baseline behavior of the acquired signal. For example, for an acquired signal having a "swinging" baseline, CDF(5,3) wavelets may be preferable to Haar wavelets, as CDF(5,3) wavelets are less likely to result in discontinuities in the soft component of the transformed signal.

FIG. 3 depicts wavelet transform step 110 as a filter bank, with wavelet coefficients 160 calculated from the difference between successive samples in the acquired signal. One of ordinary skill in the art will recognize that the block diagram of FIG. 3 depicts the use of a Haar wavelet basis.

FIG. 3 also depicts a thresholding step 150. Wavelet coefficients above a separation threshold are assigned to the hard component of the transformed signal, while wavelet coefficients below the separation threshold are assigned to the soft component of the transformed signal. Determination of the separation threshold is described in detail below.

As seen in FIG. 3, the hard component of the transformed signal is reconstructed without notch filtering in block 130. On the other hand, the soft component of the transformed signal is both reconstructed (block 140a) and notch filtered (block 140b) in block 140. As shown in FIG. 3, the notch filter is applied in the time domain; as discussed above, however, the order of blocks 140a and 140b could be reversed, such that the notch filter is applied in the wavelet domain, without departing from the scope of the present invention.

The algorithm illustrated in the block diagram of FIG. 3 can also be described mathematically. Let $\{h(j)\}$ denote an orthogonal wavelet basis. Then any wave $u_j$ can be expanded into the wavelet basis:

$$u_j = \langle u \rangle + w(j) \sum_i \tilde{u}_i \cdot h_i(j), \quad (1)$$

where [u] is the average value of the wave, tilde (~) denotes corresponding wavelet coefficients, $h_i(j)$ are the components of the j's wavelet basis vector, and w(j) are scale dependent weights. Without loss of generality, one can assume that the weights are positive. The weights in the wavelet transform play a role in efficient implementation by allowing avoidance of factors of $\sqrt{\sqrt{2}}$ present in the normalized Haar and other bases, thus advantageously reducing the complexity of the computation.

Thresholding step 170 can be described by the expression:

$$\text{if } \tilde{u}_i \leq th_i \text{ then } \tilde{S}u_i = \tilde{u}_i \text{ else } \tilde{R}u_i = \tilde{u}_i, \quad (2)$$

where $th_i$ is a set of thresholds, $\tilde{S}u_i$ describes the soft component of the signal, and $\tilde{R}u_i$ describes the hard component of the signal. In the preferred embodiments of the invention, all thresholds are the same and are based upon a statistical property of either the acquired signal or, preferably, a statistical property of the transformed signal, as described in further detail below.

Reconstructed parts of the signal are given by the equations:

$$Su_j = \sum_i \tilde{S}u_i \cdot h_i(j) \cdot w_i \quad (3)$$

$$Ru_j = \langle u \rangle + \sum_i \tilde{R}u_i \cdot h_i(j) \cdot w_i,$$

where Suj and Ruj are, correspondingly, the soft and hard components of the signal.

The soft component may then be notch filtered and recombined with the hard component:

$$\text{filtered}(u) = Ru + \text{notch}(Su), \quad (4)$$

where filtered(u) is the final result of filtration (e.g., the output signal), and notch(Su) is the result of applying the notch filter to the reconstructed soft component.

As described above, the wavelet coefficients are compared to a separation threshold in step 170 in order to separate the wavelet coefficients into the hard component (e.g., the wavelet coefficients higher than the separation threshold) and the soft component (e.g., the wavelet coefficients lower than the separation threshold). If the separation threshold is set too high, too much of the acquired signal will be separated into the hard component, and, recalling that only the soft component is notch filtered, no notch filter is effectively applied. On the other hand, if the separation threshold is set too low, the sharp spikes of the acquired signal will be separated into the soft component, and, recalling that the interaction of sharp peaks with a notch filter often leads to ringing, ringing may persist in the output signal. Determination of an appropriate separation threshold in the wavelet domain, therefore, is an aspect of the present invention.

Because signals may have differing properties, such as amplitude and noise content, it is desirable to be able to automatically determine a suitable separation threshold. The inventor has observed that, for any signal, there is a range of suitable separation thresholds for which significant reduction in ringing will occur. This is desirable, as it permits the present invention to perform advantageously even when the properties of the acquired signal vary over time.

As described above, the separation threshold is preferably based upon a statistical property of either the acquired signal or the transformed signal. More preferably, it is based upon a statistical property of the transformed signal. In some embodiments of the invention, the separation threshold is based upon the standard deviation of either the acquired signal or the transformed signal. For example, if interference constitutes the majority of the standard deviation, then the separation threshold could be established as the standard deviation ("STD") multiplied by a factor m, which may be experimentally determined for different types of signals, according to the equation:

$$\text{th} = m * \text{STD}. \quad (5)$$

Because signal properties (whether of the acquired signal or the transformed signal) may vary in time, it is desirable to compute the standard deviation in a moving window. For signals related to cardiac activity, the moving window is preferably about two cardiac cycles, or about two seconds, wide.

Computations of standard deviation in a moving window may be computationally expensive. Preferably, therefore, the separation threshold is based upon a moving average of the wavelet coefficients. The most preferable moving average is an exponential moving average. The exponential moving average for a variable $u_i$ is defined as:

$$\bar{u}_{i+1} = (1-\lambda)\bar{u}_i + \lambda u_i, \quad (6)$$

where $\bar{u}_i$ is the exponential moving average and $\lambda$ is known as the "forgetting factor." The forgetting factor is preferably chosen such that the effective window size within which the exponential moving average is calculated is about the same as the effective window size that would be used in a conventional moving average. For example, where the conventional moving average would be calculated in a window about two seconds wide and a sampling rate of 1200 Hz, a suitable forgetting factor is $1/2400$.

The computation can be made even more efficient by replacing the standard deviation with the moving average of the area under the curve of the transformed signal, which may be defined as:

$$STA = \overline{\text{abs}(u_i - \bar{u}_i)}. \quad (7)$$

In this case, Equation (5) can be modified as follows:

$$\text{th} = m * STA, \quad (8)$$

with the factor m (also referred to as a "forgetting factor") being different from the value of m utilized with the standard deviation (Equation (6)). For Equation (8), a suitable forgetting factor m is about 10.

It is also contemplated that the separation threshold may be computed in the time domain. Where the separation threshold is computed in the wavelet domain, the contribution of the smooth component is preferably excluded from the computation, as it reflects baseline movement not relevant to the filtration process. In the time domain, these baseline changes are rejected via the choice of an appropriate forgetting factor $\lambda$.

One of ordinary skill in the art will recognize that the present invention will introduce latency equal to the latency of the wavelet filter plus the latency of the notch filter. Thus, it may be desirable to compensate for latency introduced by the wavelet filter, the notch filter, or both the wavelet filter and the notch filter.

FIG. 3 illustrates a latency compensation step 180 that compensates for latency introduced by the notch filter by applying a delay $z_0$ to the reconstructed hard component. If there is no latency introduced by the notch filter, $z_0$ may be set to zero.

Even where the latency of the notch filter is zero, the latency of the output signal will be equal to the latency of the wavelet filter, which is the same as the number of samples used in the wavelet transform computation. In systems that simultaneously display multiple signals in real-time, some of which are not delayed by the wavelet filter latency, it may be desirable to compensate for the wavelet filter latency. In some embodiments of the invention, this is accomplished by delaying all signals by the same number of samples, adjusting the delay of the filtered waveforms accordingly.

Additional methods of compensating for latency will be described with reference to FIGS. 4 and 5, which are block diagrams of alternative methods of isolating or extracting an interference signal from the soft component of the transformed signal according to the present invention.

Figure 4:
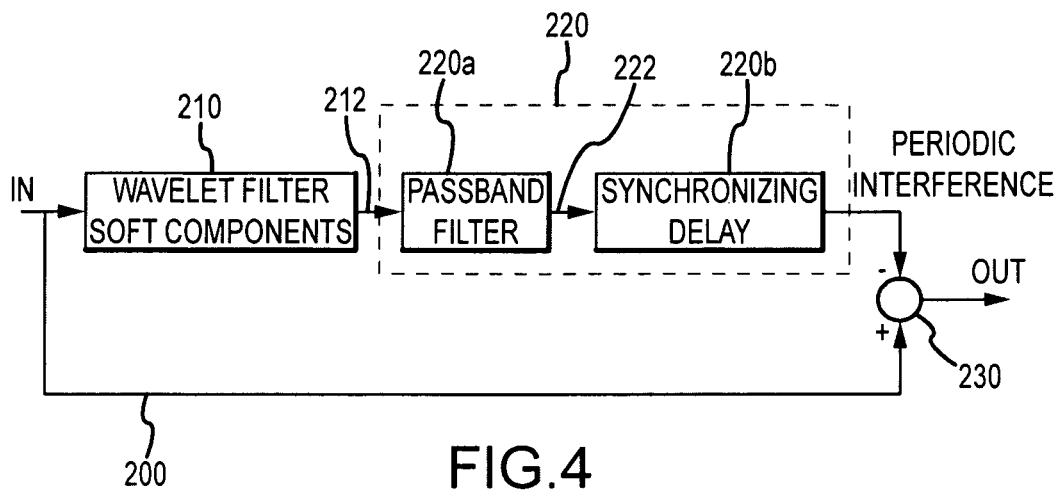
FIG. 4 is a block diagram of another embodiment of a filtration method according to the present invention.

Referring first to FIG. 4, there is shown a block diagram of a method that exploits the periodic nature of the interference signal to filter the acquired signal in a manner that does not introduce additional latency. The acquired signal is represented by line 200 in FIG. 4. In block 210, the acquired signal is transformed into the wavelet domain and the soft component of the transformed signal is extracted via application of the separation threshold. In block 220, the soft component (line 212) is band-pass filtered (block 220a) to isolate the interference signal (line 222). For example, the band-pass filter may be a 60 Hz band-pass filter that has a pass band between about 59 Hz and about 61 Hz. The soft component is also subjected to a synchronizing delay (block 220b) in order to ensure that the isolated interference signal is in phase with the noise in the acquired signal. Though only one block 220 is depicted in FIG. 4, it is contemplated that multiple, parallel blocks 220 may be used for each of a plurality of harmonics of the noise in the acquired signal. In block 230, the isolated and in-phase interference signal is subtracted from the acquired signal in order to produce the output signal (e.g., the acquired signal with the noise removed).

Figure 5:
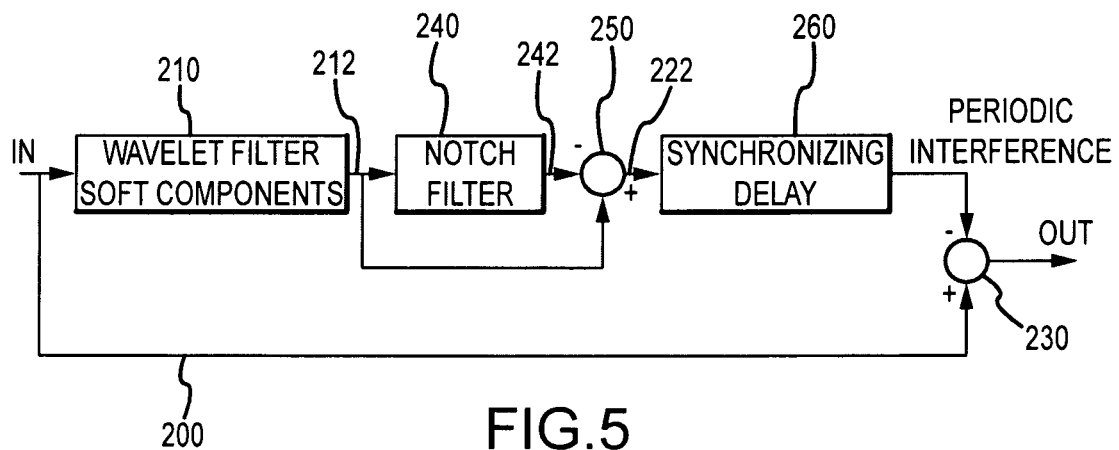
FIG. 5 is a block diagram of still another embodiment of a filtration method according to the present invention.

FIG. 5 is a block diagram of a preferred method of isolating the interference signal in the soft component of the transformed signal. Rather than subjecting the soft component (line 212) to a band-pass filter, it is subjected to a notch filter (e.g., a 60 Hz notch filter) in block 240 to output a notch filtered soft component (line 242). In block 250, the notch filtered soft component is subtracted from the unfiltered soft component, such that the output of block 250 is the isolated interference signal. In block 260, the isolated interference signal is brought in phase with the noise in the acquired signal. Block 230 again represents subtracting the isolated and in-phase interference signal from the acquired signal in order to produce the output signal (e.g., the acquired signal with the noise removed).

The methods described above may be executed by one or more computer systems, and may be software implemented (e.g., one or more software programs executed by one or more computer systems of processors), hardware implemented (e.g., a series of instructions stored in one or more solid state devices), or a combination of both. The computer may be a conventional general purpose computer, a special purpose computer, a distributed computer, or any other type of computer. Further, the computer may comprise one or more processors, such as a single central processing unit or a plurality of processing units, commonly referred to as a parallel processing environment. The term "processor" as used herein refers to a computer microprocessor and/or a software program (e.g., a software module or separate program) that is designed to be executed by one or more microprocessors running on one or more computer systems.

For example, a system for filtering an electrophysiological signal may include: a signal acquisition device, such as an ECG or EGM, to acquire a signal indicative of electrophysiological activity; a wavelet transformation processor that transforms the acquired signal (e.g., the ECG or EGM) into the wavelet domain; a first filtering processor that extracts a soft component from the transformed signal; a second filtering processor that isolates an interference signal from the soft component; and a signal reconstruction processor that produces an output signal corresponding to the acquired signal filtered to eliminate the interference signal. As described above, the second filtering processor may apply a band-pass filter or a notch filter to the soft component of the transformed signal in order to isolate the interference signal. In other embodiments of the invention, a third filtering processor extracts a hard component from the transformed signal. It is contemplated, of course, that any or all of the processors can be combined (e.g., the same filtering processor may extract both the hard component and the soft component from the transformed signal).

By way of further example, each of the processes and decisions identified in FIGS. 2-5 can be implemented using one or more computer processors running on one or more computer systems, thereby establishing a computerized system and method for the present invention.

Although several embodiments of this invention have been described above with a certain degree of particularity, those skilled in the art could make numerous alterations to the disclosed embodiments without departing from the spirit or scope of this invention.

For example, though the methods described above adjust the phase of the isolated interference signal, it is contemplated that the phase of the acquired signal could be adjusted instead of or in addition to adjusting the phase of the isolated interference signal in order to subtract the isolated interference signal from the acquired signal.

As another example, though FIG. 5 depicts only a single notch filter, it is contemplated that multiple notch filters could be used in sequence for a plurality of harmonics of the noise in the acquired signal.

As still another example, it is contemplated that both the hard component and the soft component may be filtered through either the same or different filters. To this end, it is within the spirit and scope of the invention to utilize notch filters, band-pass filters, high-pass filters, low-pass filters, and the like at any suitable frequency or frequencies for a particular application of the present teachings.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of filtering an electrophysiological signal, the method comprising:
   acquiring a signal indicative of electrophysiological activity;
   inputting the signal indicative of electrophysiological activity to signal processing hardware, and, using the signal processing hardware:
   applying a wavelet transform to transform the acquired signal into the wavelet domain;
   applying a wavelet filter to separate the transformed signal into a hard component and a soft component;
   reconstructing the hard component into the time domain;
   reconstructing the soft component into the time domain; and
   combining the reconstructed hard component and the reconstructed soft component into an output signal.

2. The method according to claim 1, further comprising applying a notch filter to the soft component.

3. The method according to claim 2, wherein the step of applying a notch filter to the soft component comprises applying a notch filter to the reconstructed soft component.

4. The method according to claim 2, wherein the step of applying a notch filter to the soft component precedes the step of reconstructing the soft component.

5. The method according to claim 1, wherein the step of applying a wavelet filter to separate the transformed signal comprises:
determining a separation threshold;
assigning portions of the transformed signal having wavelet coefficients above the separation threshold into the hard component; and
assigning portions of the transformed signal having wavelet coefficients below the separation threshold into the soft component.

6. The method according to claim 5, wherein the separation threshold is determined based upon a statistical property of the acquired signal.

7. The method according to claim 5, wherein the separation threshold is determined based upon a statistical property of the transformed signal.

8. The method according to claim 5, wherein the separation threshold is determined based upon a moving average of the standard deviation of the transformed signal.

9. The method according to claim 8, wherein a signal window within which the moving average of the standard deviation is calculated is about two cardiac cycles wide.

10. The method according to claim 5, wherein the separation threshold is determined based upon a moving average of the wavelet coefficients.

11. The method according to claim 10, wherein the separation threshold is determined based upon an exponential moving average of the wavelet coefficients.

12. The method according to claim 11, wherein a forgetting factor of the exponential moving average is selected such that an effective window within which the exponential moving average is calculated is at least about two seconds wide.

13. The method according to claim 5, wherein the separation threshold is determined based upon a moving average of the area under the curve of the transformed signal multiplied by a forgetting factor.

14. The method according to claim 13, wherein the forgetting factor is about 10.

15. The method according to claim 1, wherein the step of applying a wavelet transform comprises applying a wavelet transform utilizing Haar wavelets.

16. The method according to claim 1, wherein the step of applying a wavelet transform comprises applying a wavelet transform utilizing CDF (5,3) wavelets.

17. The method according to claim 1, further comprising compensating for latency introduced by at least one filter.

18. The method according to claim 17, wherein the step of compensating for latency comprises compensating for latency in a notch filter by applying a latency delay to the reconstructed hard component prior to combining the reconstructed hard component and the reconstructed soft component.

19. A method of filtering an electrophysiological signal, comprising:
acquiring a signal indicative of electrophysiological activity;
inputting the signal indicative of electrophysiological activity to signal processing hardware, and, using the signal processing hardware:
applying a wavelet transform to transform the acquired signal into the wavelet domain;
applying a wavelet filter to separate the transformed signal into a hard component and a soft component;
applying a notch filter to the soft component; and
combining the hard component and the filtered soft component into an output signal.

20. A method of filtering an electrophysiological signal, comprising:
acquiring a signal indicative of electrophysiological activity;
inputting the signal indicative of electrophysiological activity to signal processing hardware, and, using the signal processing hardware:
applying a wavelet transform to transform the acquired signal into the wavelet domain;
applying a wavelet filter to extract a soft component from the transformed signal;
applying a filter to the soft component to isolate an interference signal; and
producing an output signal comprising the acquired signal filtered to eliminate the interference signal.

21. The method according to claim 20, further comprising adjusting at least one of the interference signal and the acquired signal such that the interference signal and the acquired signal are in phase.

22. The method according to claim 20, wherein:
the step of applying a filter to the soft component to isolate an interference signal comprises applying a band-pass filter to the soft component to produce the interference signal; and
the step of producing an output signal comprises subtracting the interference signal from the acquired signal.

23. The method according to claim 20, wherein:
the step of applying a filter to the soft component to isolate an interference signal comprises:
applying a notch filter to the soft component; and
subtracting an output of the notch filter from the soft component to produce the interference signal; and
the step of producing an output signal comprises subtracting the interference signal from the acquired signal.

24. The method according to claim 20, wherein:
the step of applying a wavelet filter to extract a soft component from the transformed signal further comprises extracting a hard component from the transformed signal;
the step of applying a filter to the soft component to isolate an interference signal comprises applying a notch filter to the soft component; and
the step of producing an output signal comprises combining the hard component with the filtered soft component.

25. A method of filtering an electrophysiological signal, the method comprising:
acquiring a signal indicative of electrical activity in cardiac tissue;
inputting the signal indicative of electrical activity in cardiac tissue to signal processing hardware, and, using the signal processing hardware:
applying a wavelet transform to transform the acquired signal into the wavelet domain;
applying a wavelet filter to extract a soft component from the transformed signal;
applying a filter to the soft component to extract an interference signal;
adjusting the interference signal to be in phase with the acquired signal; and
subtracting the adjusted interference signal from the acquired signal to produce an output signal.

26. The method according to claim 25, wherein the filter applied to the soft component is a band-pass filter.

27. The method according to claim 26, wherein the steps of applying a filter to the soft component to extract an interference signal and adjusting the interference signal to be in phase with the acquired signal are repeated for each of a plurality of harmonics of the interference signal.

28. The method according to claim 25, wherein the filter applied to the soft component is a notch filter.

29. A system for filtering an electrophysiological signal, comprising:
   a signal acquisition device configured to acquire a signal indicative of electrophysiological activity;
   a wavelet transformation processor that transforms the acquired signal into the wavelet domain;
   a first filtering processor that extracts a soft component from the transformed signal;
   a second filtering processor that isolates an interference signal; and
   a signal reconstruction processor that produces an output signal comprising the acquired signal filtered to eliminate the interference signal.

30. The system according to claim 29, wherein the second filtering processor applies a band-pass filter to the transformed signal and outputs the interference signal.

31. The system according to claim 29, wherein the second filtering processor applies a notch filter to the soft component of the transformed signal, subtracts an output of the notch filter from the soft component of the transformed signal, and outputs the interference signal.

32. The system according to claim 29, further comprising a third filtering processor that extracts a hard component from the transformed signal, and wherein:
   the second filtering processor applies a notch filter to the soft component of the transformed signal; and
   the signal reconstruction processor combines the hard component of the transformed signal with the notch filtered soft component.

* * * * *